United States Patent
Sethuraman et al.

(10) Patent No.: US 12,076,190 B2
(45) Date of Patent: Sep. 3, 2024

(54) SYSTEMS AND METHODS FOR GUIDED ULTRASOUND DATA ACQUISITION

(71) Applicant: KONINKLIJKE PHILIPS N.V., Eindhoven (NL)

(72) Inventors: Shriram Sethuraman, Lexington, MA (US); Sergei Y. Shulepov, Eindhoven (NL); Sabina Manzari, Eindhoven (NL); Nico Maris Adriaan De Wild, Eindhoven (NL); Krishnamoorthy Palanisamy, Bangalore (IN); Denny Mathew, Eindhoven (NL); Rick Bezemer, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 206 days.

(21) Appl. No.: 17/298,040

(22) PCT Filed: Dec. 3, 2019

(86) PCT No.: PCT/EP2019/083400
§ 371 (c)(1),
(2) Date: May 28, 2021

(87) PCT Pub. No.: WO2020/115005
PCT Pub. Date: Jun. 11, 2020

(65) Prior Publication Data
US 2022/0096053 A1   Mar. 31, 2022

(30) Foreign Application Priority Data
Dec. 17, 2018 (EP) .................................. 18212911

(51) Int. Cl.
*A61B 8/00* (2006.01)
*A61B 8/08* (2006.01)

(52) U.S. Cl.
CPC ............ *A61B 8/483* (2013.01); *A61B 8/0891* (2013.01); *A61B 8/4488* (2013.01);
(Continued)

(58) Field of Classification Search
CPC ..... A61B 8/483; A61B 8/0891; A61B 8/4488; A61B 8/4494; A61B 8/461; A61B 8/488;
(Continued)

(56) References Cited

U.S. PATENT DOCUMENTS

| | | | |
|---|---|---|---|
| 5,474,073 A | * | 12/1995 | Schwartz ............ G01S 7/52077 600/456 |
| 5,997,479 A | | 12/1999 | Savord |

(Continued)

FOREIGN PATENT DOCUMENTS

WO    2005006954 A2    1/2005

OTHER PUBLICATIONS

International Search Report and Written Opinion of PCT/EP2019/083400, dated Jan. 20, 2020.

*Primary Examiner* — Alexei Bykhovski (57) ABSTRACT

The invention provides a method for guiding the acquisition of ultrasound data. The method begins by obtaining ultrasound data from a plurality of data acquisition planes and performing spatial registration of the data acquisition planes. A number of vessels are then identified in each data acquisition plane. A location of a vessel bifurcation is then identified based on the spatial registration of the data acquisition planes and the number of vessels in each data acquisition plane. A guidance instruction is generated based on the location of the vessel bifurcation, wherein the guidance instruction is adapted to indicate a location to obtain further ultrasound data.

19 Claims, 8 Drawing Sheets

(52) U.S. Cl.
CPC ............ *A61B 8/4494* (2013.01); *A61B 8/461* (2013.01); *A61B 8/488* (2013.01); *A61B 8/5207* (2013.01)

(58) Field of Classification Search
CPC ..... A61B 8/5207; A61B 8/469; A61B 8/4245; A61B 8/463; G01S 7/52066; G01S 15/8915
See application file for complete search history.

(56) References Cited

U.S. PATENT DOCUMENTS

| | | | |
|---|---|---|---|
| 6,013,032 | A | 1/2000 | Savord |
| 6,283,919 | B1 | 9/2001 | Roundhill |
| 6,443,896 | B1 | 9/2002 | Detmer |
| 6,458,083 | B1 | 10/2002 | Jago |
| 6,530,885 | B1 | 3/2003 | Entrekin |
| 6,623,432 | B2 | 9/2003 | Powers |
| 8,929,622 | B2 * | 1/2015 | Galigekere ............... G06T 7/90 382/128 |
| 2006/0056672 | A1 | 3/2006 | Barth |
| 2008/0188752 | A1 * | 8/2008 | Randall .................. A61B 8/463 600/455 |
| 2012/0296214 | A1 * | 11/2012 | Urabe .................. A61B 8/4444 600/447 |
| 2014/0081142 | A1 | 3/2014 | Toma |
| 2014/0303499 | A1 | 10/2014 | Toma |
| 2014/0371593 | A1 | 12/2014 | Kondoh |
| 2015/0238165 | A1 | 8/2015 | Hyuga |
| 2016/0157814 | A1 * | 6/2016 | Palanisamy ............ A61B 8/483 600/454 |
| 2018/0125376 | A1 * | 5/2018 | Denney, Jr ............ A61B 5/085 |

\* cited by examiner

SYSTEMS AND METHODS FOR GUIDED ULTRASOUND DATA ACQUISITION

CROSS-REFERENCE TO PRIOR APPLICATIONS

This application is the U.S. National Phase application under 35 U.S.C. § 371 of International Application No. PCT/EP2019/083400, filed on Dec. 3, 2019, which claims the benefit of U.S. Provisional Patent Application Ser. No. 62/774,921, filed Dec. 4, 2018 and European Patent Application No. 18212911.4, filed on Dec. 17, 2018. These applications are hereby incorporated by reference herein.

FIELD OF THE INVENTION

The invention relates to the field of ultrasound, and in particular to the field of guiding the acquisition of ultrasound data.

BACKGROUND OF THE INVENTION

A complete ultrasound examination of a blood vessel involves a combination of structural imaging (B-mode) and Doppler imaging (color flow and/or spectral Doppler data). An expert sonographer knows where to look for the vessel of interest and performs a coordinated set of workflow steps to complete the exam. As an example, in the case of a carotid artery evaluation, the most common approach involves an initial B-mode sweep along the neck of a subject to locate the arteries, identify the carotid bifurcation and note any visual structural abnormalities in the vessel wall. Further, flow abnormality, arterial pulsatility and flow directionality are visualized using color Doppler flow measurements. Clinically, these procedures are part of a typical workflow with visual feedback (in the form of ultrasound images) provided on an ultrasound monitor.

However, there exist healthcare settings and applications where it is not practical to use any ultrasound image feedback that would normally be used in a traditional ultrasound examination. In addition, the operator may not possess sufficient skill in performing ultrasound imaging in order to accurately place an ultrasound sensor or to make adjustments that ensure the quality of the obtained data.

This is particularly the case in the context of medical interventions involving continuous patient monitoring where ultrasound derived parameters may provide additional information on a patient monitor. For example, a traditional ultrasound exam workflow and analysis is not possible in peri-operative care where non-ultrasound personnel are involved and where regular ultrasound scanners are not practical for prolonged, operator-free monitoring.

In ultrasound diagnostic imaging, typical Doppler measurements performed on the vessel are performed by skilled sonographers, wherein the sonographer positions a measurement plane in the middle of the vessel and along the main axis.

However, locating such a plane in a vessel by non-skilled operator can be cumbersome. Moreover, in operating room or intensive care environments, image feedback on a monitor may not be available. Therefore, the placing of the sensor would need to be performed in the absence of the actual ultrasound image of a vessel.

There is therefore a need for a means to guide the placement of an ultrasound sensor in the absence of traditional monitor based feedback, without requiring significant additional hardware.

SUMMARY OF THE INVENTION

The invention is defined by the claims.

According to examples in accordance with an aspect of the invention, there is provided a method for guiding the acquisition of ultrasound data, the method comprising:
  obtaining ultrasound data, said ultrasound data comprising Doppler ultrasound data, from a plurality of data acquisition planes;
  performing spatial registration on the plurality of data acquisition planes;
  identifying a number of vessels in each data acquisition plane, wherein said identifying comprises determining a direction of blood flow within the data acquisition planes based on the Doppler ultrasound data;
  determining a location of a vessel bifurcation based on the spatial recognition of the plurality of data acquisition planes and the number of vessels in each data acquisition plane;
  generating a guidance instruction based on the location of the vessel bifurcation, wherein the guidance instruction is adapted to indicate a location to obtain further ultrasound data.

The method provides for guiding a user to locate an ultrasound transducer at an optimal position for blood flow measurement.

In the example of the carotid artery, the blood flow is best measured at a position below the confluence of the interior carotid artery and the exterior carotid artery (i.e. below the bifurcation).

By locating where the number of vessels changes from one (common carotid) to two (interior carotid and exterior carotid), the bifurcation of the carotid artery may be located. This may then be used to guide the placement of the ultrasound transducer at an optimal location. Including Doppler ultrasound data in the ultrasound data to be assessed enables correcting for motion within the data acquisition planes during the identification of blood vessels. The Doppler ultrasound data may assist in distinguishing certain vessels within the field of view based on the determined direction of the blood flow. In this way, the direction of the blood flow may be used to identify certain vessels within the field of view. Further, negligible blood flows from minor vessels may be discounted to improve the accuracy of the determinations.

This method may be employed on any suitable medical device capable of communicating with a transducer.

In an embodiment, the method further comprises:
  identifying a central axis of a vessel based on the ultrasound data, wherein:
    the guidance instruction is further based on the central axis of the vessel; and
    the location to obtain further ultrasound data comprises an inclined data acquisition plane, wherein the inclined data acquisition plane is inclined relative to the central axis of the vessel.

In this way, the further ultrasound data is obtained by way of an inclined data acquisition plane.

Having an inclined plane with respect to the central axis of the vessel results in a more accurate and reliable measurement of the blood flow in that plane.

In a further embodiment, the inclined data acquisition plane defines an angle in the range of 10 to 50 degrees with the central axis of the vessel.

In this way, the accuracy of the further ultrasound data acquired after the guidance may be improved.

In an embodiment, the method further comprises identifying a vessel cross section based on the ultrasound data.

In a further embodiment, the performing of the spatial registration on the plurality of data acquisition planes is based on the identified vessel cross section.

In an embodiment, the identifying of a number of vessels in each data acquisition plane is based on the identified vessel cross section.

In an arrangement, the Doppler ultrasound data comprises pulsatility data.

In this way, it is possible to identify the blood vessels within the data acquisition planes according to the observed variance in blood flow velocity.

In an embodiment, the guidance instruction comprises one or more of:
an audible instruction;
a visual instruction;
an electronic control signal; and
a tactile instruction.

This provides for a variety of ways in which an instruction may be delivered to a user or an automated system.

In an embodiment, the ultrasound data comprises ultrasound image data.

In this way, the user may view the ultrasound data as an ultrasound image.

According to examples in accordance with an aspect of the invention, there is provided a computer program comprising computer program code means which is adapted, when said computer program is run on a computer, to implement the method described above.

According to examples in accordance with an aspect of the invention, there is provided a medical system adapted to guide the acquisition of ultrasound data, the system comprising:

a processor, wherein the processor is adapted to:
obtain ultrasound data, said ultrasound data comprising Doppler ultrasound data, from a plurality of data acquisition planes;
perform spatial registration on the plurality of data acquisition planes;
identify a number of vessels in each data acquisition plane, wherein said identifying comprises determining a direction of blood flow within the data acquisition planes based on the Doppler ultrasound data;
determine a location of a vessel bifurcation based on the spatial registration of the plurality of data acquisition planes and the number of vessels in each data acquisition plane; and
generate a guidance instruction based on the location of the vessel bifurcation, wherein the guidance instruction is adapted to indicate a location to obtain further ultrasound data.

In an embodiment, the system further comprises an ultrasound transducer in communication with the processor, wherein the ultrasound transducer is adapted to acquire ultrasound data from a plurality of data acquisition planes.

In a further embodiment, the ultrasound transducer comprises one or more of:
a linear transducer array;
a T-shaped transducer array; and
a 2D transducer array.

A linear transducer array offers a simple implementation of the system. A T-shaped array provides for obtaining ultrasound data in two orthogonal planes without requiring the manual manipulation of the ultrasound transducer during acquisition. A 2D array provides for a full ultrasound scan of the area of interest to be performed automatically and the guidance may simply select the transducers to activate in the subsequent data acquisition.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for guiding the acquisition of ultrasound data. The method begins by obtaining ultrasound data from a plurality of data acquisition planes and performing spatial registration of the data acquisition planes. A number of vessels are then identified in each data acquisition plane. A location of a vessel bifurcation is then identified based on the spatial registration of the data acquisition planes and the number of vessels in each data acquisition plane. A guidance instruction is generated based on the location of the vessel bifurcation, wherein the guidance instruction is adapted to indicate a location to obtain further ultrasound data.

Figure 1:
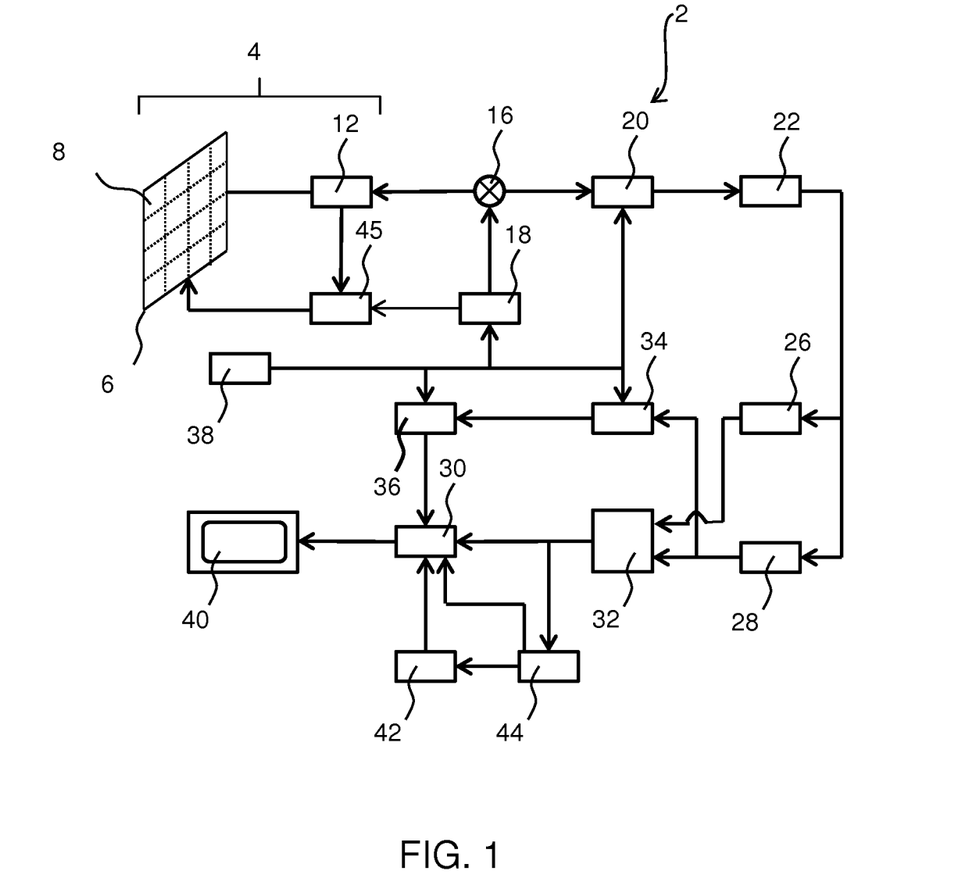
FIG. 1 shows an ultrasound diagnostic imaging system to explain the general operation.

The general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.). The volume renderer 42 may also perform a segmentation function, thereby allowing to perform anatomy segmentation on the acquired ultrasound data.

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
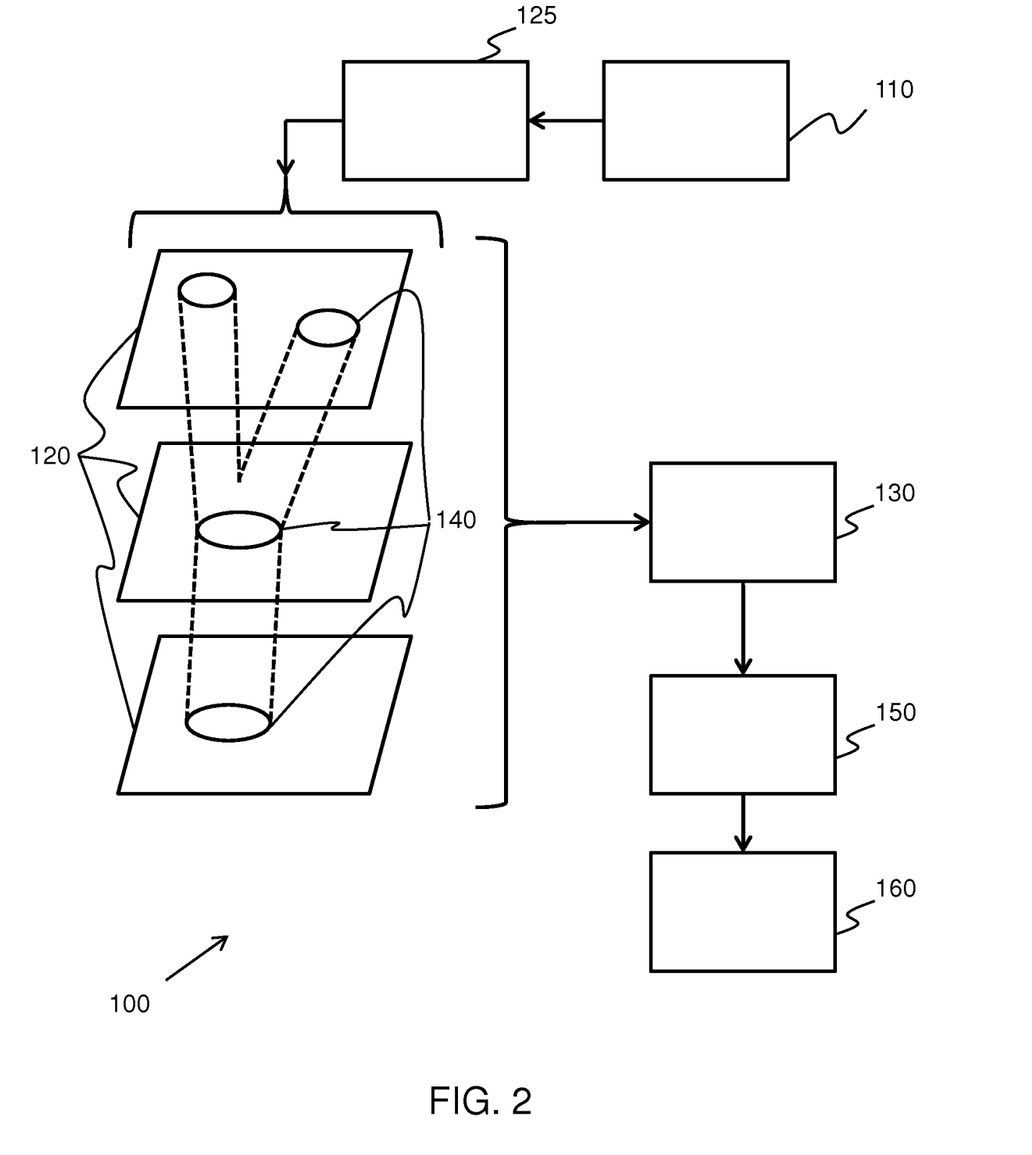
FIG. 2 shows a method of the invention.

FIG. 2 shows a method 100 for guiding the acquisition of ultrasound data.

The method begins in step 110, wherein ultrasound data is obtained from a plurality of data acquisition planes 120.

In step 125, spatial registration is performed on the plurality of data acquisition planes. In other words, the location of each data acquisition plane, relative to the other data acquisition planes, is determined. The spatial registration may be performed based on vessel cross sections identified in the data acquisition planes. Alternatively, markers may be placed on the subject, which may then be used to identify the locations of the data acquisition planes. Further alternatives that may be used for plane registration with respect to an anatomy could include positional sensors, accelerometers, gyroscopes, EM tracking sensors, optical tracking sensors and the like.

In step 130, a number of vessels 140 are identified in each data acquisition plane. In the example shown in FIG. 2, two of the data acquisition planes 120 contain one vessel 140 and one data acquisition plane contains two vessels.

The vessels in each data acquisition plane may be identified in a number of ways. For example, the identification of the number of vessels may include identifying a vessel cross section based on the ultrasound data.

The ultrasound data may include a variety of data. For example, the ultrasound data may include ultrasound image data, which may then be used to represent the data acquisition planes as 2D ultrasound images. Further, image segmentation may be employed to recognize and identify vessel cross sections.

Ultrasound image data may include structural B-mode data, which may not be displayed as an image to a user but may be employed in a process internal to the ultrasound system.

Further, the ultrasound data may include Doppler ultrasound data. In this case, the identification of the number of vessels in each data acquisition plane may include determining a direction of blood flow within the data acquisition planes based on the Doppler ultrasound data.

The direction of blood flow within a data acquisition plane, and more specifically within a given area of a data acquisition plane, may be used to identify vessels. For example, where a data acquisition plane is located at a neck of a subject, two vessels (the carotid artery and the jugular vein) may be identified by way of their opposing flow directions.

Further, or alternatively, the ultrasound data may include pulsatility data, which represents the variance of the blood flow velocity within a given vessel. In the example of pulsatility data, the vessels may be identified by way of matching the captured pulsatility data to known pulsatility profiles, such as the typical pulsatility profile of a carotid artery or jugular vein.

The combination of ultrasound image data (B-mode data) and Doppler (color) data may be referred to as duplex data-based vessel identification.

Various methods of vessel identification are discussed further below.

In step 150, a location of a vessel bifurcation is determined based on the ultrasound data and the number of vessels in each data acquisition plane.

For example, a location of a bifurcation may be identified based on a change in the number of vessels present in the data acquisition planes. As shown in FIG. 2, the number of vessels in the data acquisition planes changes from two vessels to one vessel, meaning that a vessel bifurcation may exist within the data acquisition region. The existence of a vessel bifurcation may be confirmed through the use of Doppler color ultrasound data, pulsatility data or further ultrasound image data.

In step 160, a guidance instruction is generated based on the location of the vessel bifurcation, wherein the guidance instruction is adapted to indicate a location to obtain further ultrasound data. Examples of the guidance instruction are discussed further below.

This method may be carried out within an ultrasound system, such as the system described above with reference to FIG. 1. However, this method may also be employed on any device that is capable of receiving ultrasound data. For example, an ultrasound probe may be used to acquire the ultrasound data, which may then be provided to a separate patient monitor to carry out the method described above. The data may be provided by any suitable communication means.

Figure 3:
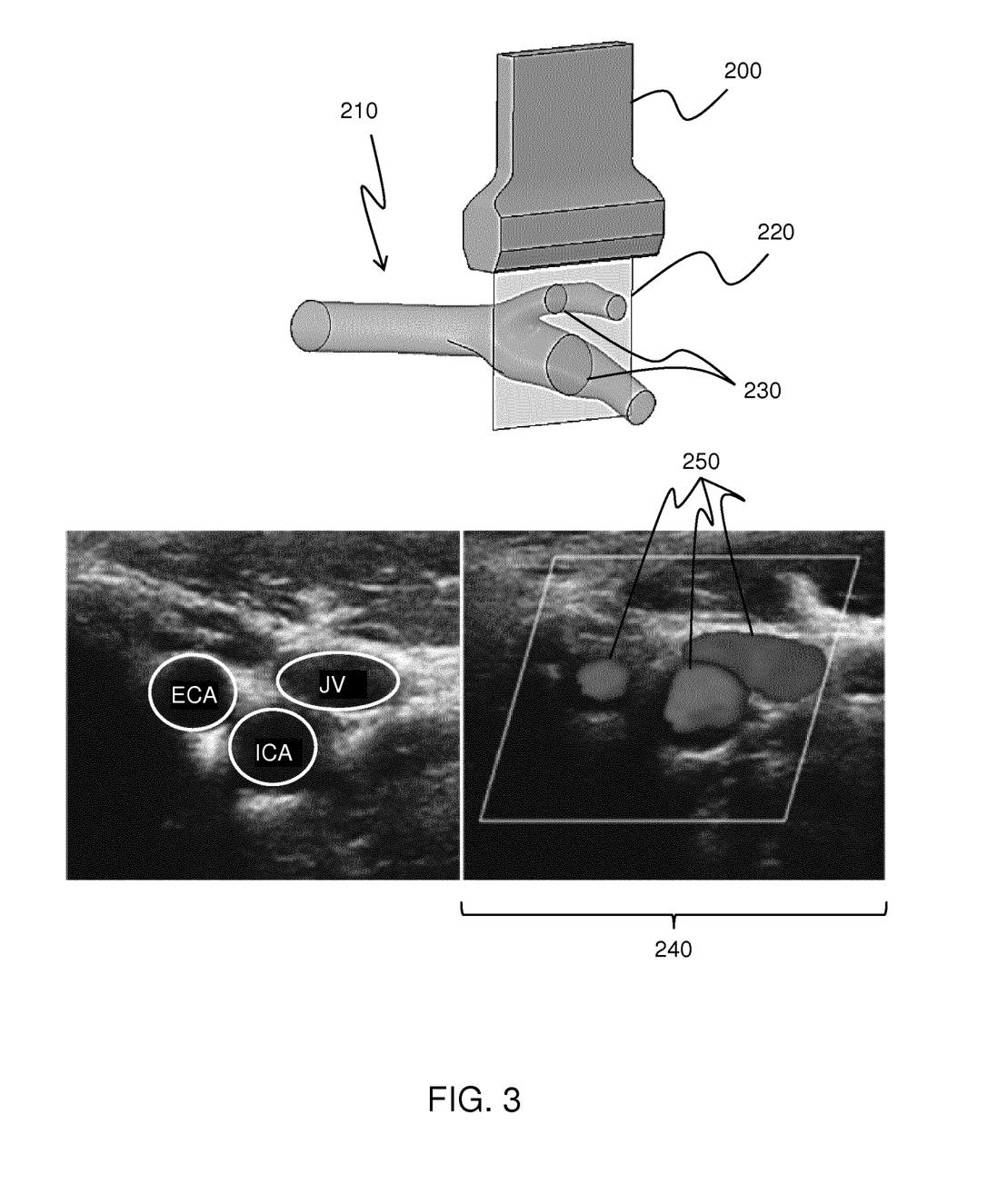
FIG. 3 shows an example of a data acquisition plane.
Figure 4:
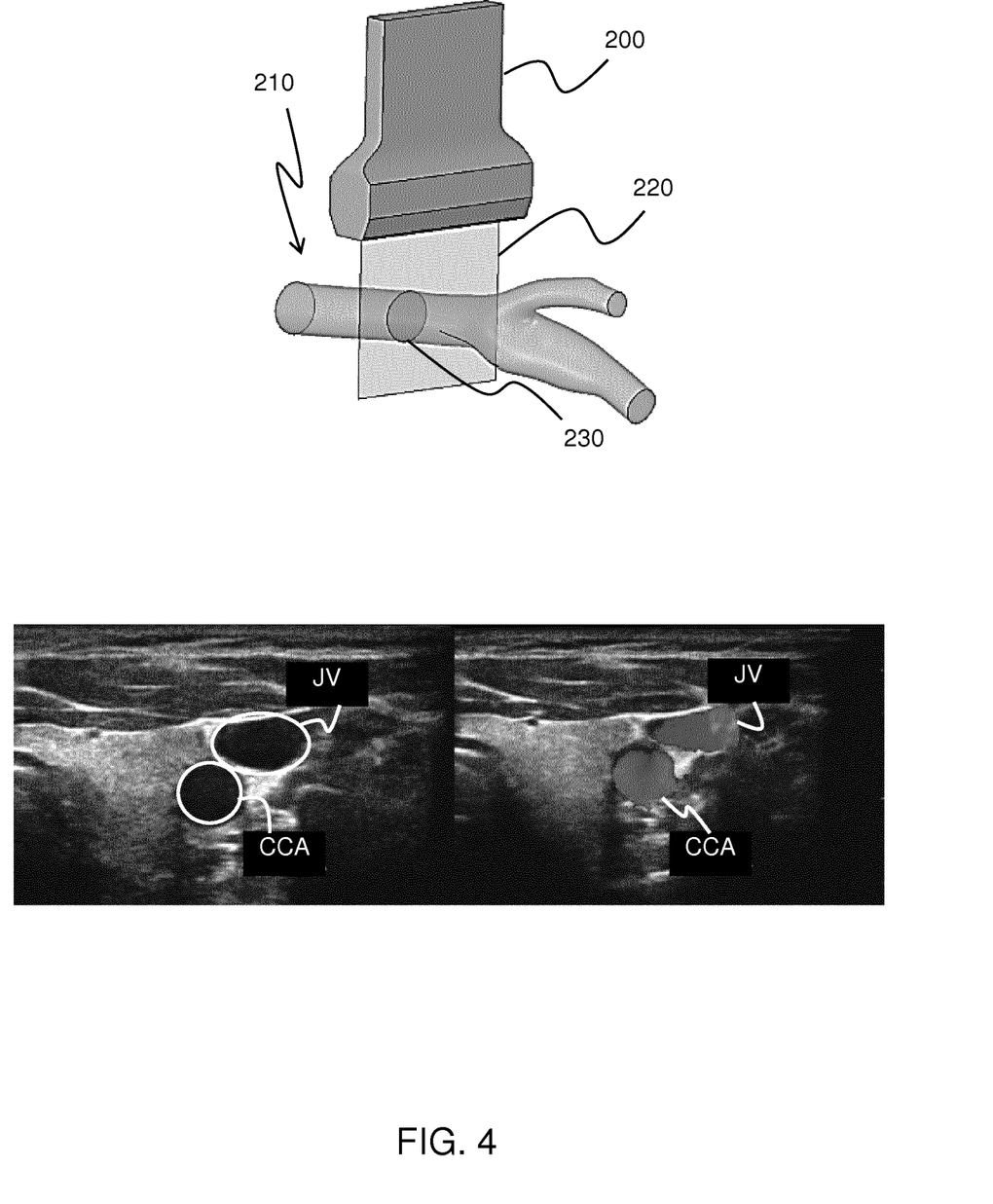
FIG. 4 shows a further example of a data acquisition plane.

FIGS. 3 and 4 show an example of a data acquisition plane wherein the ultrasound data comprises both ultrasound image data, in the form of B-mode data, and Doppler color data. In this example, a linear ultrasound transducer array 200 is used to acquire data relating to the carotid artery 210 of a user. The current data acquisition plane 220 and vessel cross sections 230 within said plane are shown.

In FIG. 3, the transducer array 200 is placed proximate to an upper part of the carotid artery and moved (which may be a guided movement) to find multiple vessels. In this case, the vessel finding algorithm is based on a combination 240 of B-mode image data and a color Doppler data stream, wherein shape recognition may be applied to both the B-mode data and the color data. In this way, it is possible to identify the internal carotid artery ICA, the external carotid artery ECA and the jugular vein JV based on the roughly circular or elliptical shapes in either the B-mode data or the color data.

The B-mode data and the color data may be used to discriminate the artery and the vein from each other. Further, it is possible to implement a hardware implementation to discriminate between the artery and vein using information about direction of the flow with respect to the ultrasound sensor. In this case, the placement of the transducer array should be realized with a certain orientation with respect the vessels being imaged, which may be indicated on the sensor. By analyzing the color flow information number of vessels as well as their type such as the artery and vein may then be separated.

By way of an example, a vessel may be identified according to the following steps. Firstly, the color Doppler flow image is converted to HSV (Hue, Saturation, Value) space and the image is converted to a binary image by applying threshold saturation to HSV space. The binary image is then pre-processed by filling the holes in the image and the region having the largest area within the image is selected by way of connected component analysis.

The center of a vessel is identified from the centroid of the selected region and the RGB patterns of the selected region are analyzed to differentiate the laminar and turbulent flow within the vessel. Indeed, depending on the medical application this information may be used as a guide to maintain a current position or to move away from the bifurcation. A pulsatility measure is then computed from the Doppler color signal to confirm that the signal is from a given vessel, such as an artery.

In FIG. 4, the transducer array is moved to the opposite side of the bifurcation area. Ideally, one ellipse representing a vessel will be in the color Doppler data stream at this moment. If, as is shown in FIG. 4, the jugular vein is in the field of view, it may be discriminated as described above and rejected for measurement.

Figure 5:
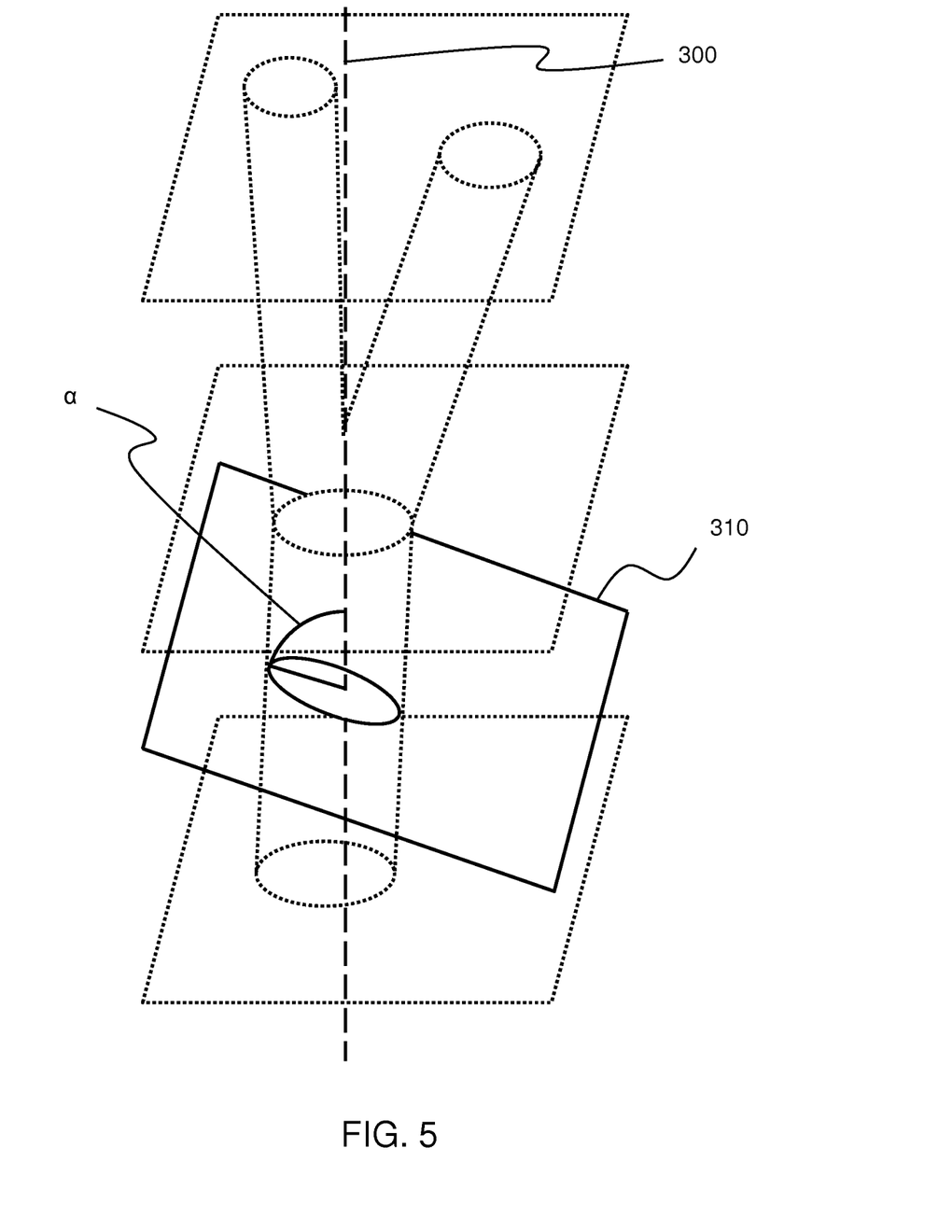
FIG. 5 shows a schematic representation of data acquisition planes.

FIG. 5 shows a schematic representation of a data acquisition plane for obtaining the further ultrasound data following a guidance instruction.

In this example, the method shown in FIG. 2 further comprises identifying a central axis 300 of a vessel based on the ultrasound data. As discussed above, the ultrasound data may include one or more of ultrasound image data, color Doppler data or pulsatility data.

Accordingly, the guidance instruction for locating the position for further ultrasound data acquisition may also be based on the central axis of the vessel. In the example shown in FIG. 5, the location to obtain further ultrasound data comprises an inclined data acquisition plane 310, which is inclined relative to the central axis of the vessel by an angle α. Angle α may be in the range of 10 to 50 degrees, for example between 15 and 45 degrees, with the central axis of the vessel.

In this way, the ultrasound sensor used to acquire the ultrasound data does not need to be aligned with the vessel at a given specific angle, which may be difficult to achieve in practice. Rather, the sensor may be placed at an angle within the range of 10 to 50 degrees with respect the central axis of the vessel and achieve optimal data acquisition results. In this way, the positioning of a sensor becomes very robust towards patient motion and is not susceptible to the same sensitivity as a traditional ultrasound data acquisition method. Further, the elimination of the requirement to place the sensor in a specific orientation reduces the time and skill required to properly locate the probe for data acquisition.

The angle of orientation of the probe may be determined by the ultrasound system based on the elliptical shape of the vessel. For example, a thin ellipse may indicate a small angle α; whereas, a near circular shape may indicate a larger angle α.

Figure 6:
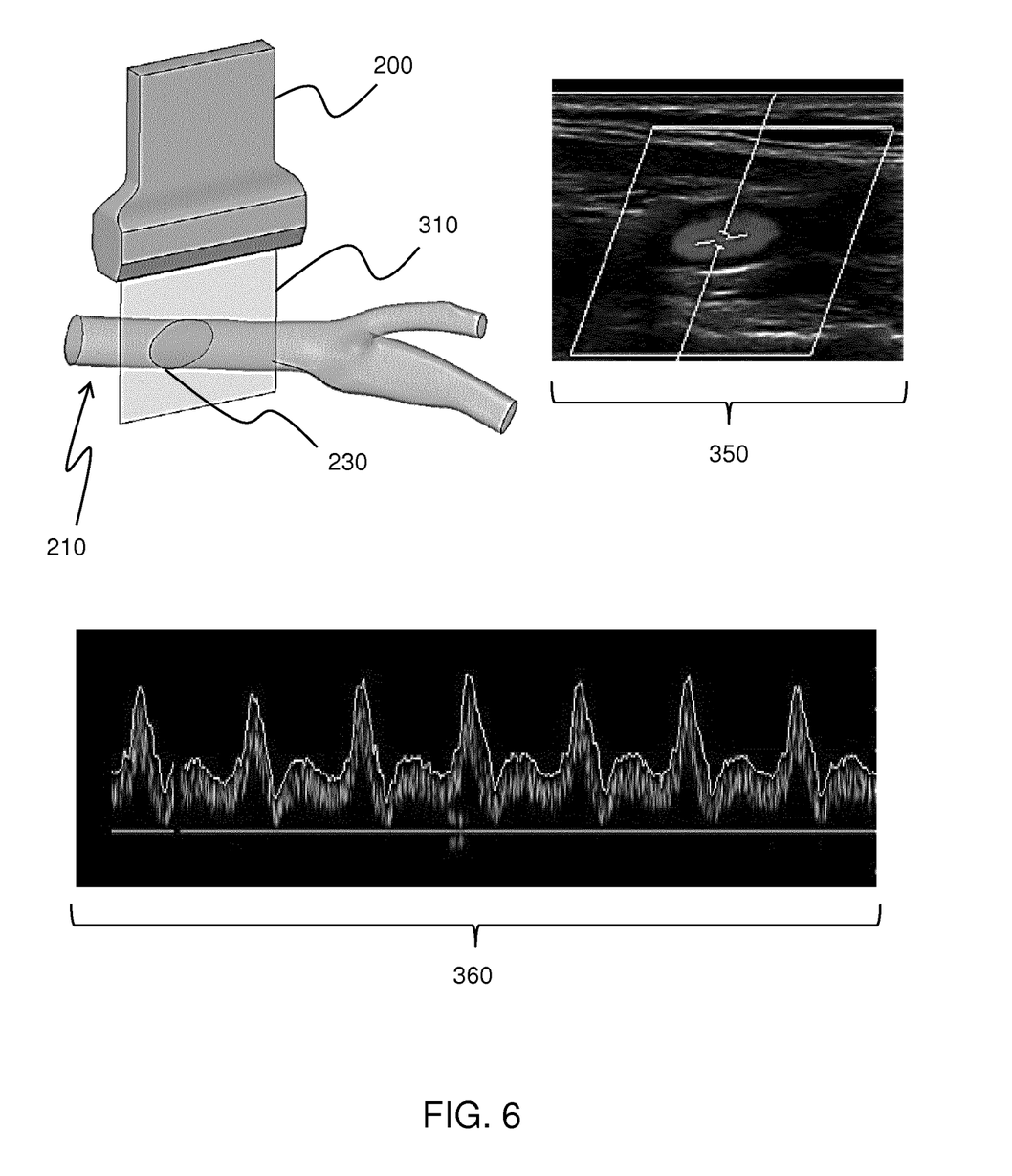
FIG. 6 shows a schematic representation of a sensor collecting data from an inclined data acquisition plane.

FIG. 6 shows a schematic representation of a sensor 200 collecting data from an inclined data acquisition plane 310. In this case, combined color Doppler and B-mode data 350 is acquired alongside a graph of pulsatility data 360.

The graph of the pulsatility data shows a plot of blood velocity within the vessel (on the y-axis) against time (on the x-axis). As can be seen from the graph, the plot covers approximately seven cardiac cycles, wherein each peak represents a constriction of the heart. The pulsatility data may be used in the identification of a vessel.

In summary, the algorithms presented above are suitable for real-time monitoring of full beat-to-beat waveforms representing blood velocity and flow within a vessel. Together with real-time segmentation, the method provides for monitoring flow through the blood vessels.

As discussed above, the ultrasound data is acquired by way of a sensor. There are a number of implementations of a sensor that may be used to collect the ultrasound data as described. For example, the sensor may comprise: a linear transducer array; two linear transducer arrays, arranged such that the imaging plane of one array is orthogonal to the other; or a 2D array.

The guidance provided to the user may be provided in an indirect manner. In other words, the system may analyze the ultrasound data and generate a guidance signal by way of a guidance means separate from the sensor. For example, where a visual guidance signal is generated, an arrow may be displayed on a screen indicating a direction in which the user should move the sensor.

Alternatively, the means for providing guidance to the user may be included in the sensor itself. For example, the sensor may be adapted to generate one or more of: an audible instruction; a visual instruction; an electronic control signal; and a tactile instruction, to guide the user.

Figure 7:
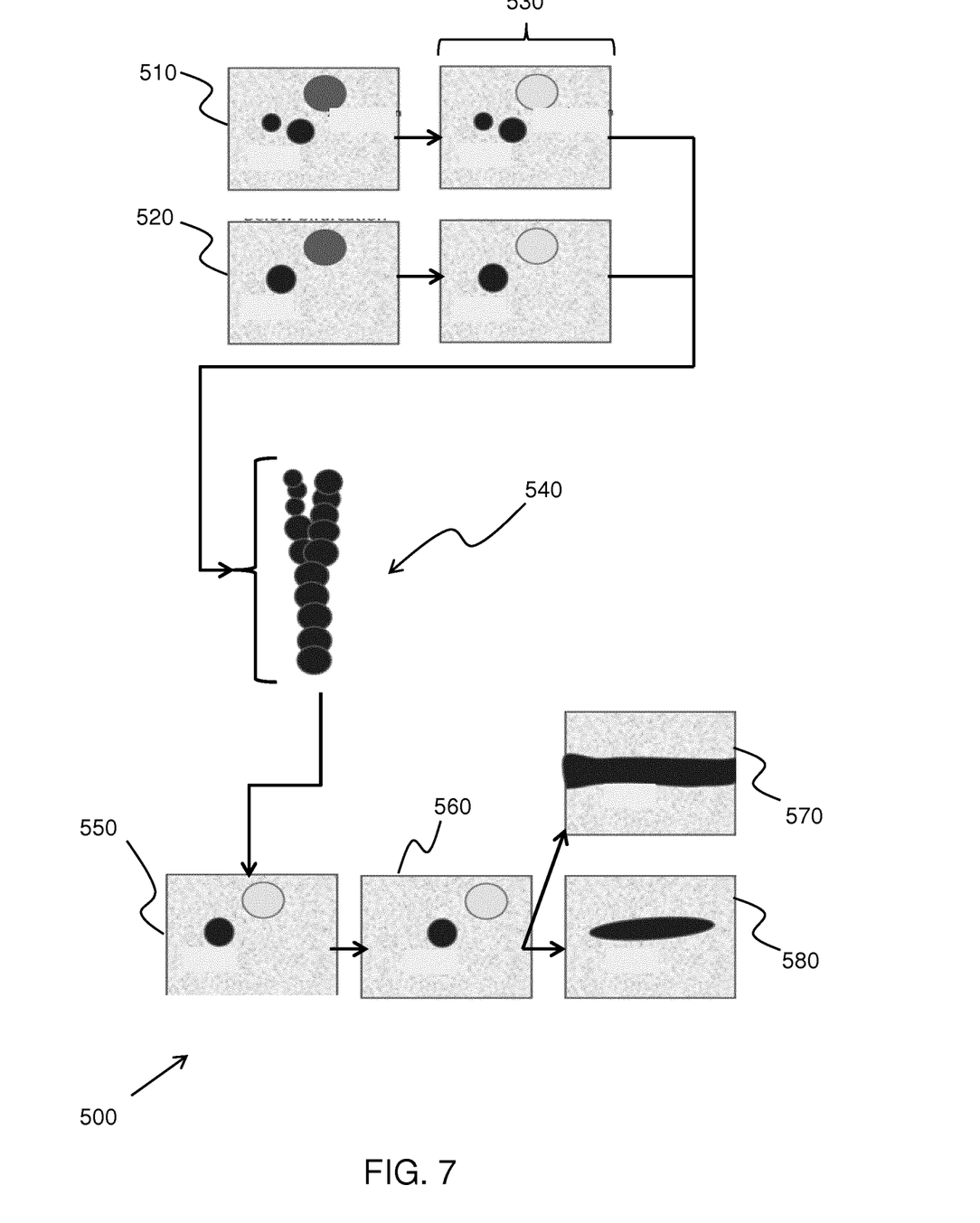
FIG. 7 shows an example workflow carried out by a sensor comprising a single linear transducer array.

FIG. 7 shows an example workflow 500 of the above methods as carried out by a sensor comprising a single linear transducer array, which may be in the form of an ultrasound patch.

Initially, ultrasound data is acquired from a plurality of data acquisition planes using the ultrasound patch. In the example shown in FIG. 7, a first data acquisition plane 510 comprises three vessels, shown by the three circles, and a second data acquisition plane 520 comprises two vessels, shown by the two circles.

Vessel identification 530 is then performed on the data acquisition planes. The vessel identification may be performed as described above. In the example shown in FIG. 7, the vessel of interest is the carotid artery, which is indicated by the black circles, and the remaining vessel, which in this case is the jugular vein, is disregarded. It may be determined through the color Doppler data and/or the pulsatility data that the two arteries in the first data acquisition plane and the one artery in the second data acquisition plane form parts of a common vessel. In other words, it may be determined that a vessel bifurcation exists between the first and second data acquisition planes.

A sweep 540 may then be performed by moving the sensor along the vessel, thereby mapping out the vessel and the bifurcation in more detail.

The ultrasound patch is then applied by a user with guidance provided by indicators. As stated, indicators may be provided on the patch, as well as, or instead of, being displayed on a remote monitor. The guidance is based on duplex ultrasound data i.e. a combination of the B-mode data and the color Doppler data. Using the duplex data, the workflow steps also make sure that the patch is placed well below the bifurcation, such that only one vessel cross section of interest exists in the data acquisition plane as shown in plane 550. For example, the patch may be placed 2 cm below the bifurcation. This ensures that the effects of turbulent flow near the bifurcation are minimized when estimating flow parameters.

The vessel of interest is then centered in the data acquisition plane as shown in plane 560. Finally, the patch is rotated such that a view along the length of the vessel is available, rather than a cross section. The length view may be a complete view 570 or a partial view 580, which may then be corrected through placement guidance or through image correction. Alternatively, the partial view 580 may be sufficient for the intended purpose, meaning that this view may act as the final position of the linear array.

In the case of visual feedback, the sensor may be provided with one or more LEDs, which may provide a visual signal to a user as to how the sensor should be moved. In the case of an audible instruction, one or more speakers may be provided to supply an audible instruction to the user. Where tactile feedback is used, the patch may be provided with one or more vibration modules, which (de)activate to provide a tactile instruction that may be interpreted by the user. In the example of an electronic instruction signal, the feedback may be provided to a remote digital means, such as a monitor, which then presents the user with an instruction in a suitable form.

Figure 8:
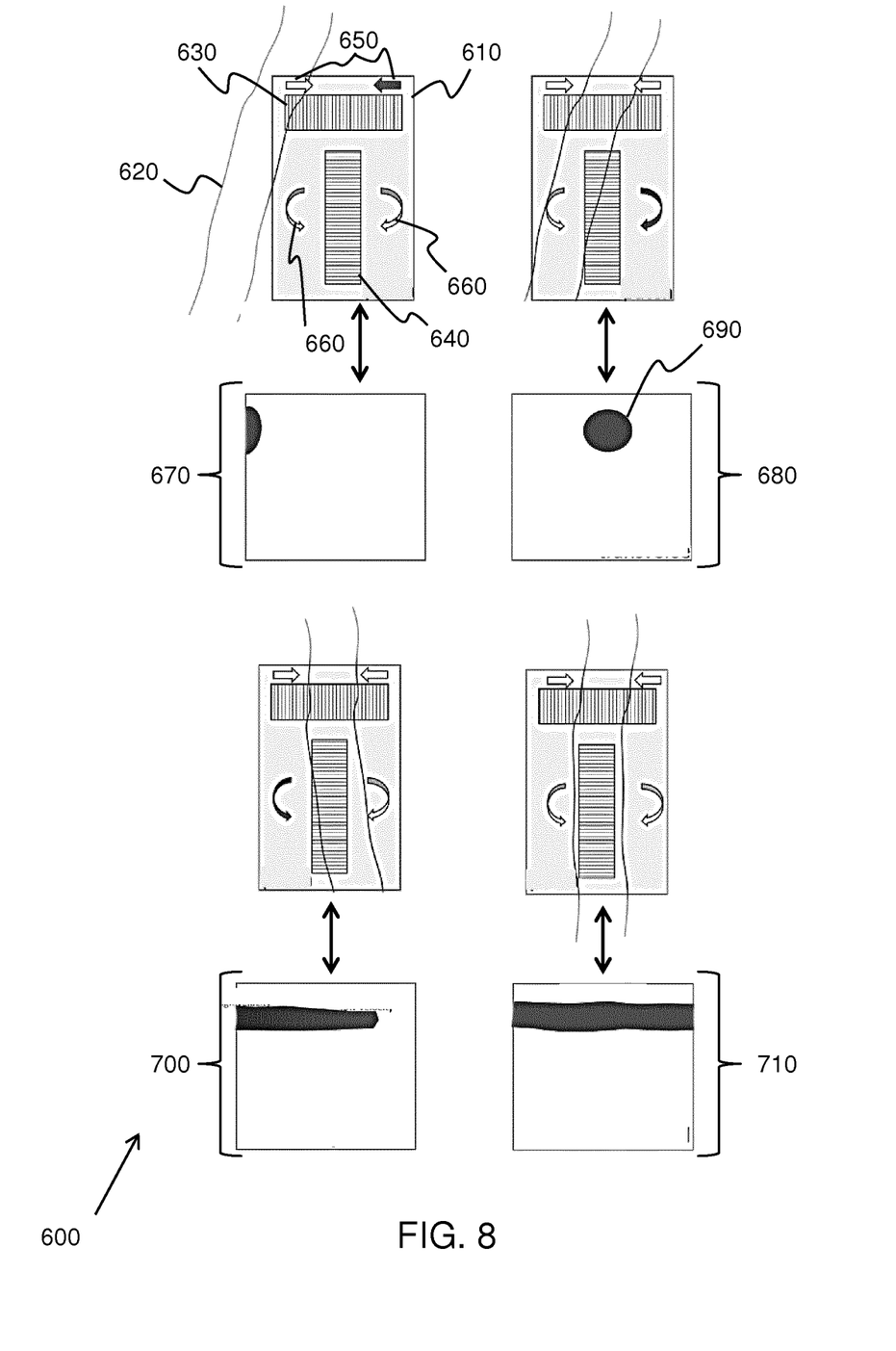
FIG. 8 shows a graphical representation of an example of guided sensor placement using a T-shaped array and visual indicators disposed on the sensor.

FIG. 8 shows a graphical representation 600 of an example of guided sensor placement using a T-shaped array and visual indicators disposed on the sensor.

A sensor 610 is shown placed in close proximity to a vessel of interest 620. The sensor comprises a first transducer array 630, which in this case generates a cross sectional view of the vessel, and a second transducer array 640 arranged orthogonally to the first transducer array. The sensor patch may also include further transducer arrays.

Further, the sensor comprises translation visual indicators 650 and rotational visual indicators 660. In operation, a translation visual indicator may be illuminated to provide a user with a guidance signal to move the patch in the indicated direction. Similarly, a rotational visual indicator may be illuminated to provide a user with a guidance signal to rotate the patch in the indicated direction.

In the example shown in FIG. 8, the sensor is placed such that the first transducer array captures a data acquisition plane that includes an incomplete view 670 of the vessel of interest. The sensor may be initialized by way of a suitable user input, for example a button located on the sensor patch.

Only the first transducer array may be activated at first in order to secure a complete cross sectional view of the vessel of interest. Alternatively, both the first and second transducer arrays may be activated simultaneously.

In this case, the ultrasound sensor patch captures duplex (B-mode and color Doppler) data, which may be streamed to a processor (in the illustrative example of FIG. 1, the image processor 30 may perform this function) of a connected ultrasound system.

A segmentation algorithm (in the illustrative example of FIG. 1, the segmentation function might be either performed by a separate unit, a volume renderer 42, or by the same processor 30, which receives the ultrasound image data), as described above, is employed to detect the vessels within the data acquisition plane on the color flow data (for example, by searching for the circular appearance of the vessels). If the vessel appears as two segmented regions then the patch is above the bifurcation. The goal in the example shown in FIG. 8 is to place the patch below the bifurcation on the common carotid artery which is a single vessel. An indicator communicates a successful completion of this step if the common carotid artery is detected. As discussed above, the segmentation can be on the color and/or the B-Mode data.

In this instance, the initial view of the vessel is incomplete. Accordingly, a translation visual indicator may be activated on the sensor patch, thereby guiding the used to move the patch to a complete view of the vessel 680.

To ensure that the segmented region 690 is indeed the desired vessel, such as an artery and not a vein or a noise artifact, the sensor may also capture pulsatility data. A pulsatile flow may be used to confirm that the signal is from the desired vessel.

When a complete cross section of the desired vessel is captured a control switch may activate the second transducer array 640 to begin streaming duplex ultrasound data from along the length of the vessel.

An algorithm looks for a cylindrical appearance of the flow spanning the entire data acquisition plane. If the segmented vessel does not span the lateral of the data acquisition plane, there may be an angular misalignment of the sensor patch along the length of the vessel 700. The appropriate rotational visual indicators may be used to guide the user to rotate the patch and maximize the cylindrical appearance of the vessel in the ultrasound data. It should be noted that the data need not be visible to the user, but may be performed within the system by the algorithm. Once the desired view 710 is achieved, the indicators may signal the achievement of correct angular alignment. The desired view 710 may change according to the given application. For example, a view of the vessel that results in a long ellipse, rather than a full cylinder may be sufficient. Accordingly, the desired view may include a range of views of the vessel.

Switching back to the cross sectional view of the first transducer array, the algorithm may check if the vessel is still in the center of the view. A positive confirmation indicates that the elements of the second transducer array are aligned with the center axis of the vessel. Otherwise, the algorithm may instruct the user with appropriate indicators to move the sensor patch to achieve that. The user may then activate a button to signal the completion of the patch placement and the various data acquisition methods described above may proceed.

The ultrasound sensor patch may be a wearable patch that may be temporarily fixed to a subject, thereby allowing them to move freely while the patch is in operation.

In another example, the patch may include a 2D array of transducer elements capable of performing 3D ultrasound imaging. In this case, an x-plane could be used to help in vessel alignment in an analogous way to the first transducer array described above. An x-plane is suggested, rather than using the full 2D array, as this reduces the number of channels required to align the patch, which reduces the power consumption and data rate, and/or allows for higher frame rates. In this case, the patch may simply be placed on an area of interest without requiring iterative movement or adjustment of the patch. All elements of the array may be activated to find the sub-set of elements that best aligns with the vessel axis. There would be no (or minimal) training or expertise required for patch placement in such an example.

In a further example, the linear transducer arrays of the sensor patch described in FIG. 8 may be replaced with 1.5D transducer elements, which would increase the field of view of the data acquisition plane and may minimize the iterations needed to search for the vessel and/or to align the sensor patch to the vessel.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for guiding acquisition of ultrasound data, the method comprising:
   obtaining, using an ultrasound transducer, ultrasound data from a plurality of data acquisition planes, said ultrasound data comprising Doppler ultrasound data, wherein the Doppler ultrasound data comprises pulsatility data;
   performing, by a processor of a medical system in communication with the ultrasound transducer, spatial registration on the plurality of data acquisition planes;
   identifying, by the processor, a number of vessels in each of the plurality of data acquisition planes including determining a direction of blood flow within the data acquisition planes based on the Doppler ultrasound data;
   identifying, by the processor, each vessel of the number of vessels by comparing and matching the obtained pulsatility data to known pulsatility profiles for a plurality of different vessels;
   determining, by the processor comparing and matching the obtained pulsatility data to known pulsatility profiles for the plurality of different vessels, a vessel characterization of one or more of the identified number of vessels;
   determining, by the processor, a location of a vessel bifurcation based on the spatial registration of the plurality of data acquisition planes, the number of vessels in each data acquisition plane, and the characterization of one or more of the identified number of vessels;
   generating a guidance instruction based on the location of the vessel bifurcation, wherein the guidance instruction is adapted to indicate a location to obtain further ultrasound data; and
   providing the generated guidance instruction to a user of the ultrasound transducer via a user interface.

2. The method as claimed in claim 1, wherein the method further comprises:
   identifying a central axis of a vessel of the identified number of vessels based on the ultrasound data, wherein:
   the guidance instruction is further based on the central axis of the vessel; and
   the location to obtain further ultrasound data comprises an inclined data acquisition plane, wherein the inclined data acquisition plane is inclined relative to the central axis of the vessel.

3. The method as claimed in claim 2, wherein the inclined data acquisition plane defines an angle (a) in the range of 10 to 50 degrees with the central axis of the vessel.

4. The method as claimed in claim 1, wherein the method further comprises identifying a vessel cross section based on the ultrasound data.

5. The method as claimed in claim 4, wherein the performing of the spatial registration on the plurality of data acquisition planes is based on the identified vessel cross section.

6. The method as claimed in claim 4, wherein the identifying of a number of vessels in each data acquisition plane is based on the identified vessel cross section.

7. The method as claimed in claim 1, wherein the guidance instruction comprises one or more of:
   an audible instruction;
   a visual instruction;
   an electronic control signal; and
   a tactile instruction.

8. The method as claimed in claim 1, wherein the ultrasound data comprises ultrasound image data.

9. A computer program comprising computer program code means stored on a non-transitory computer readable storage medium which is adapted, when said computer program is run on a computer, to implement the method of claim 1.

10. The method as claimed in claim 1, wherein the processor utilizes a combination of B-mode image data and color Doppler data from the ultrasound data to identify the number of vessels in each data acquisition plane.

11. The method of claim 10, wherein before the processor identifies the number of vessels in each data acquisition plane, the color Doppler data is converted to Hue, Saturation, Value (HSV) space to generate a converted Doppler flow image, and the converted Doppler flow image is converted to a binary image by applying threshold saturation to the HSV space.

12. The method of claim 1, wherein the processor utilizes the pulsatility data to identify the number of vessels in each data acquisition plane.

13. The method of claim 1, wherein determining a location of a vessel bifurcation based on the spatial registration of the plurality of data acquisition planes and the number of vessels in each data acquisition plane comprises a comparison of a determined number of vessels in a first of the plurality of data acquisition planes and a determined number of vessels in a second of the plurality of data acquisition planes.

14. A medical system adapted to guide acquisition of ultrasound data, the medical system comprising:
   an ultrasound transducer in communication with a processor, wherein the ultrasound transducer is adapted to obtain ultrasound data, said data comprising Doppler ultrasound data, from a plurality of data acquisition planes, wherein the Doppler ultrasound data comprises pulsatility data;
   wherein the processor is adapted to:
   receive the ultrasound data from the ultrasound transducer;
   perform spatial registration on the plurality of data acquisition planes;
   identify a number of vessels in each data acquisition plane, said identifying including determining a direction of blood flow within the data acquisition planes based on the Doppler ultrasound data;

identify, by the processor, each vessel of the number of vessels by comparing and matching the obtained pulsatility data to known pulsatility profiles for a plurality of different vessels;

determine, by the processor comparing and matching the obtained pulsatility data to known pulsatility profiles for the plurality of different vessels, a vessel characterization of one or more of the identified number of vessels;

determine a location of a vessel bifurcation based on the spatial registration of the plurality of data acquisition planes, the number of vessels in each data acquisition plane, and the characterization of one or more of the identified number of vessels;

generate a guidance instruction based on the location of the vessel bifurcation, wherein the guidance instruction is adapted to indicate a location to obtain further ultrasound data; and a user interface configured to provide the generated guidance instruction.

15. The medical system as claimed in claim 14, wherein the ultrasound transducer comprises one or more of:

a linear transducer array;

a T-shaped transducer array; and a 2D transducer array.

16. The medical system of claim 14, wherein the processor utilizes a combination of B-mode image data and color Doppler data from the ultrasound data to identify the number of vessels in each data acquisition plane.

17. The medical system of claim 14, wherein before the processor identifies the number of vessels in each data acquisition plane, the color Doppler data is converted to Hue, Saturation, Value (HSV) space to generate a converted Doppler flow image, and the converted Doppler flow image is converted to a binary image by applying threshold saturation to the HSV space.

18. The medical system of claim 14, the processor utilizes the pulsatility data to identify the number of vessels in each data acquisition plane.

19. The medical system of claim 14, wherein determining a location of a vessel bifurcation based on the spatial registration of the plurality of data acquisition planes and the number of vessels in each data acquisition plane comprises a comparison of a determined number of vessels in a first of the plurality of data acquisition planes and a determined number of vessels in a second of the plurality of data acquisition planes.

* * * * *